US009125815B2

(12) United States Patent
Goget et al.

(10) Patent No.: US 9,125,815 B2
(45) Date of Patent: Sep. 8, 2015

(54) AGENT FOR DYEING AND/OR BLEACHING KERATINOUS FIBRES IN TWO OR MORE PARTS, COMPRISING AN ALKALINE COMPOSITION IN AN INVERSE EMULSION

(75) Inventors: Caroline Goget, Paris (FR); Gautier Deconinck, Saint-Gratien (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/518,607

(22) PCT Filed: Dec. 17, 2010

(86) PCT No.: PCT/EP2010/070024
§ 371 (c)(1),
(2), (4) Date: Apr. 9, 2013

(87) PCT Pub. No.: WO2011/076672
PCT Pub. Date: Jun. 30, 2011

(65) Prior Publication Data

US 2013/0189206 A1 Jul. 25, 2013

Related U.S. Application Data

(60) Provisional application No. 61/294,584, filed on Jan. 13, 2010.

(30) Foreign Application Priority Data

Dec. 22, 2009 (FR) ..................................... 09 59376

(51) Int. Cl.
*A61Q 5/10* (2006.01)
*A61K 8/06* (2006.01)

(52) U.S. Cl.
CPC ....................................... *A61K 8/06* (2013.01)

(58) Field of Classification Search
USPC .............. 8/405, 406, 408, 435, 580, 619, 111
See application file for complete search history.

(56) References Cited

U.S. PATENT DOCUMENTS 6,159,486 A * 12/2000 Terren et al. .................. 424/401

* cited by examiner

*Primary Examiner* — Eisa Elhilo
(74) *Attorney, Agent, or Firm* — John A. Artz; Dickinson Wright PLLC

(57) ABSTRACT

The present invention relates to an agent for dyeing and/or bleaching keratinous fibers, comprising: a water-in-oil emulsion (A) comprising one or more basifying agents, water, one or more surfactants having an HLB of less than 8, chosen from oxyalkylenated and/or glycerolated nonionic surfactants, and from 30 to 70% by weight, with respect to the total weight of the emulsion (A), of one or more oils not comprising a carboxylic acid functional group, and a second composition (B) comprising one or more oxidizing agents, the total amount of oil(s) not comprising a carboxylic acid functional group in the mixture of the emulsion (A) and of the composition (B) representing at least 20% by weight, with respect to the total weight of the mixture of these two compositions. The present invention also relates to a method for dyeing and/or bleaching keratinous fibers employing such an agent and to a kit comprising it.

15 Claims, No Drawings

AGENT FOR DYEING AND/OR BLEACHING KERATINOUS FIBRES IN TWO OR MORE PARTS, COMPRISING AN ALKALINE COMPOSITION IN AN INVERSE EMULSION

This application is a national phase application based on PCT/EP2010/070024 filed Jan. 13, 2010, which claims priority from French Application No. 0959376, filed Dec. 22, 2009, and claims the benefit of U.S. Provisional Application No. 61/294,584, filed on Jan. 13, 2010, the content of all of which is incorporated herein by reference in their entirety.

TECHNICAL FIELD

The present invention relates to an agent in two or more parts intended for the dyeing and/or bleaching of keratinous fibres, in particular human keratinous fibres, such as the hair.

BACKGROUND

Many people have sought for a long time to modify the colour of their hair and in particular to bleach it or, in contrast, to dye it, for example in order to conceal their white hair.

Essentially two types of dyeing operations have been developed in order to dye human keratinous fibres.

The first type of dyeing operation is "permanent" or "oxidation" dyeing, which employs dyeing compositions comprising oxidation dye precursors, generally known as oxidation bases. These oxidation bases are colourless or weakly coloured compounds which, in combination with oxidizing products, can give rise, by an oxidative condensation process, to coloured compounds.

It is also known that it is possible to vary the shades obtained with these oxidation bases by combining them with couplers or colouring modifiers. The variety of the molecules involved as oxidation bases and couplers makes it possible to obtain a rich palette of colours.

The second type of dyeing operation is "semipermanent" dyeing or direct dyeing, which consists in applying direct dyes to the keratinous fibres, direct dyes being coloured and colouring molecules having an affinity for the said fibres, in leaving to stand and in then rinsing them.

In order to carry out these dyeing operations, the direct dyes generally employed are chosen from nitrobenzene, anthraquinone, nitropyridine, azo, xanthene, acridine, azine or triarylmethane direct dyes.

This type of process does not require the use of an oxidizing agent in order to develop the colouring. However, it is possible to employ such an agent in order to obtain a lightening effect with the dyeing operation. Reference is then made to a direct or semipermanent dyeing operation under lightening conditions.

Permanent or also semipermanent dyeing methods under lightening conditions thus consist in employing, with the dyeing composition, an aqueous composition comprising at least one oxidizing agent, under alkaline pH conditions in the great majority of cases.

The role of this oxidizing agent is to decompose the melanin of the hair, which, depending on the nature of the oxidizing agent present, results in a more or less pronounced lightening of the fibres. Thus, for a relatively slight lightening, the oxidizing agent is generally hydrogen peroxide. When greater lightening is desired, use is normally made of peroxygenated salts, such as, for example, persulphates, in the presence of hydrogen peroxide.

In order to improve the performances of the methods for dyeing and/or bleaching human keratinous fibres and to limit the inconveniences related to the use of alkaline agents and of oxidizing agents, the proposal has been made to employ, in the dyeing compositions, a substantial amount of one or more fatty substances.

However, the incorporation in these compositions of a sufficient amount of fatty substance proves to be problematic, all the more so when the dyeing composition is formulated in the form of a conventional emulsion of oil-in-water type. This is because these formulations are thermodynamically unstable and their viscosity changes over time, all the more so if the amount of fatty substance is high.

SUMMARY OF THE INVENTION

The Applicant has now discovered that the act of employing an alkaline composition in the form of an inverse water-in-oil emulsion, comprising well defined proportions of oil, in the presence of certain lipophilic surfactants, makes it possible to incorporate a large amount of oily compounds in the compositions applied to the fibres, while retaining the stability of these compositions.

A subject-matter of the present invention is thus an agent for dyeing and/or bleaching keratinous fibres, comprising:

- a water-in-oil emulsion (A) comprising one or more basifying agents, water, one or more surfactants having an HLB of less than 8, chosen from oxyalkylenated and/or glycerolated nonionic surfactants, and from 30 to 70% by weight, with respect to the total weight of the emulsion (A), of one or more oils not comprising a carboxylic acid functional group, and
- a second composition (B) comprising one or more oxidizing agents, the total amount of oil(s) not comprising a carboxylic acid functional group in the mixture of the emulsion (A) and of the composition (B) representing at least 20% by weight, with respect to the total weight of the mixture of these two compositions.

More specifically, a subject-matter of the present invention is an agent for dyeing and/or bleaching keratinous fibres, comprising a first composition (A) composed of a water-in-oil inverse emulsion comprising one or more lipophilic surfactants and one or more basifying agents and optionally one or more dyes and a second composition (B) comprising one or more oxidizing agents.

The present invention also relates to a multicompartment device comprising the dyeing and/or bleaching agent according to the invention.

Finally, a subject-matter of the present invention is a method for dyeing and/or bleaching keratinous fibres employing the agent according to the invention.

When the agent according to the invention is intended for the dyeing, optionally lightening dyeing, of keratinous fibres, the emulsion (A) additionally comprises one or more oxidation dyes and/or one or more direct dyes.

Conversely, when the agent according to the invention is intended for just the bleaching of the keratinous fibres, the emulsion (A) and the composition (B) do not comprise direct dye or oxidation dye (bases and couplers) or else, if they are present, their total content does not exceed 0.005% by weight, with respect to the weight of each composition. This is because, at such a content, only the composition would be dyed, that is to say that no effect of dyeing the keratinous fibres would be observed.

The emulsion (A) of the dyeing and/or bleaching agent according to the present invention is stable and its viscosity does not change or changes only slightly over time.

In addition, when it is intended for the dyeing of keratinous fibres, the agent according to the invention is particularly effective especially as regards the uptake of the dyes onto the fibres, the power and the chromaticity of the colouring obtained, and the selectivity of the colouring along the same fibre or between fibres sensitized to different extents.

When it is intended for the bleaching of keratinous fibres, the agent according to the invention exhibits a lightening performance equivalent to, indeed even better than, that obtained with the existing compositions, in particular with those based on ammonium hydroxide.

The agent according to the invention also exhibits the advantage of limiting offensive odours during its preparation or its application on the fibres.

Other characteristics and advantages of the invention will become more clearly apparent on reading the description and examples which follow.

DESCRIPTION OF THE PREFERRED EMBODIMENTS

In that which will follow and unless otherwise indicated, the limits of a range of values are included within this range.

The human keratinous fibres treated by the method according to the invention are preferably the hair.

According to the present invention, the emulsion (A) comprises one or more basifying agents.

The basifying agent can in particular be an inorganic or organic base.

Preferably, the basifying agent is chosen from aqueous ammonia, alkaline carbonates, sodium hydroxide, potassium hydroxide, organic amines, such as, for example, alkanolamines and their derivatives, and the compounds of following formula (I):

(I)

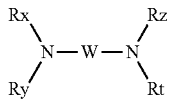

in which W is a $C_1$-$C_6$ alkylene residue optionally substituted by a hydroxyl group or a $C_1$-$C_6$ alkyl radical and Rx, Ry, Rz and Rt, which are identical or different, represent a hydrogen atom or a $C_1$-$C_6$ alkyl, $C_1$-$C_6$ hydroxyalkyl or $C_1$-$C_6$ aminoalkyl radical.

Mention may be made, as examples of such compounds of formula (I), of 1,3-diaminopropane, 1,3-diamino-2-propanol, spermine or spermidine.

The basifying agents which are particularly preferred are alkanolamines, in particular mono-, di- and triethanolamines.

In a preferred alternative form of the invention, the basifying agent is monoethanolamine.

According to a specific embodiment, the emulsion (A) comprises, as basifying agent, at least one organic amine, preferably at least one alkanolamine. When the emulsion (A) comprises several basifying agents, including an alkanolamine and aqueous ammonia or one of its salts, the organic amine or amines are preferably predominant by weight, with respect to the amount of ammonia present in the emulsion (A).

According to a preferred embodiment of the present invention, the emulsion (A) does not comprise aqueous ammonia.

According to an embodiment which is also preferred of the present invention, when the emulsion (A) comprises aqueous ammonia, it also comprises one or more alkanolamines and the amount by weight of alkanolaminc(s) in the emulsion (A) is greater than the amount by weight of ammonia in this same emulsion.

Generally, the emulsion (A) exhibits a content of basifying agent(s) ranging from 0.1 to 40% by weight, preferably from 0.5 to 20% by weight, with respect to the weight of this emulsion.

Preferably, the emulsion (A) and/or the aqueous phase of the emulsion (A) exhibits a pH of greater than or equal to 8 and more preferably a pH ranging from 8.5 to 11.5.

This pH can also be adjusted to the desired value by the use, in addition to the basifying agent, of one or more acidifying agents.

Mention may be made, among the acidifying agents, by way of example, of inorganic or organic acids, such as hydrochloric acid, orthophosphoric acid, sulphuric acid, carboxylic acids, such as acetic acid, tartaric acid, citric acid or lactic acid, or sulphonic acids.

The emulsion (A) is provided in the form of an inverse emulsion of water-in-oil type.

The water-in-oil emulsions or inverse emulsions according to the invention are true emulsions and should be distinguished from microemulsions, which, in contrast to true emulsions, are thermodynamically stable systems.

The size of the droplets of the dispersed phase of the water-in-oil emulsions of the invention is preferably between 10 nm and 100 μm and preferably between 200 nm and 50 μm. The size is the D(3,2) mean diameter, which can be measured in particular using a laser particle sizer.

The inverse emulsion (A) can be prepared by conventional processes for the preparation of inverse emulsions well known to a person skilled in the art.

The emulsion (A) comprises water.

According to a first alternative form, the amount of water can range from 5 to 70% by weight, better still from 10 to 50% by weight, with respect to the total weight of the emulsion (A).

According to a second alternative form, the aqueous phase comprising water and the compounds soluble in water at ambient temperature and at atmospheric pressure represents from 10 to 70% by weight, better still from 15 to 50% by weight, with respect to the total weight of the emulsion (A).

The emulsion (A) also comprises from 30 to 70% by weight of one or more oils not comprising a carboxylic acid functional group and preferably from 40 to 65% by weight, with respect to the total weight of the emulsion (A).

The term "oil" is understood to mean, within the meaning of the present invention, an organic compound which is insoluble in water at normal temperature (25° C.) and at atmospheric pressure (760 mm Hg; i.e. $1.013\times10^5$ Pa), that is to say which exhibits a solubility in water of less than 5% by weight, preferably of less than 1% by weight and more preferably still of less than 0.1% by weight. These compounds exhibit, in their structure, at least one hydrocarbon chain comprising at least 6 carbon atoms or a sequence of at least two siloxane groups. In addition, the oils are soluble in organic solvents under the same temperature and pressure conditions, such as, for example, chloroform, ethanol or benzene. Furthermore, oils are liquid at normal temperature (25° C.) and at atmospheric pressure (760 mm Hg; i.e. $1.013\times10^5$ Pa).

The term "oil not comprising a carboxylic acid functional group" denotes an oil not comprising a —COOH group or a —$COO^-$ group.

The oil or oils not comprising a carboxylic acid functional group are chosen in particular from hydrocarbons, non-silicone oils of animal, vegetable, mineral or synthetic origin, fatty alcohols, fatty acid and/or fatty alcohol esters, silicones, and their mixtures.

It is specified that, within the meaning of the invention, the fatty alcohols and fatty acids more particularly exhibit one or more saturated or unsaturated and linear or branched hydrocarbon groups comprising from 6 to 30 carbon atoms which are optionally substituted, in particular by one or more hydroxyl groups (in particular from 1 to 4). If they are unsaturated, these compounds can comprise from 1 to 3 conjugated or nonconjugated carbon-carbon double bonds.

More particularly, the liquid hydrocarbons are chosen from:

- linear or branched and optionally cyclic lower $C_6$-$C_{16}$ alkanes. Mention may be made, by way of example, of hexane, undecane, dodecane, tridecane or isoparaffins, such as isohexadecane, isododecane and isodecane.
- linear or branched hydrocarbons of mineral, animal or synthetic origin of more than 16 carbon atoms, such as liquid paraffins, liquid petrolatum, polydecenes, hydrogenated polyisobutenes, such as Parléam®, or squalane.

In a preferred alternative form, the liquid hydrocarbon or hydrocarbons are chosen from liquid paraffins and liquid petrolatum.

Preferably, the silicones are chosen from liquid polydialkylsiloxanes, in particular liquid polydimethylsiloxanes (PDMSs), and liquid polyorganosiloxanes comprising at least one aryl group.

These silicones can also be organomodified. The organomodified silicones which can be used in accordance with the invention are liquid silicones as defined above which comprise, in their structure, one or more organofunctional groups attached via a hydrocarbon group.

The organopolysiloxanes are defined in more detail in the work by Walter Noll, "Chemistry and Technology of Silicones" (1968), Academic Press. They can be volatile or non-volatile.

When they are volatile, the silicones are chosen more particularly from those having a boiling point of between 60° C. and 260° C. and more particularly still from:

(i) cyclic polydialkylsiloxanes comprising from 3 to 7 and preferably from 4 to 5 silicon atoms. They are, for example, octamethylcyclotetrasiloxane, sold in particular under the name of Volatile Silicone® 7207 by Union Carbide or Silbione® 70045 V2 by Rhodia, decamethylcyclopentasiloxane, sold under the name of Volatile Silicone® 7158 by Union Carbide and Silbione® 70045 V5 by Rhodia, dodecamethylcyclohexasiloxane, sold under the name of Silsoft 1217 by Momentive Performance Materials, and their mixtures.

Mention may also be made of cyclocopolymers of the dimethylsiloxane/methylalkylsiloxane type, such as Silicone Volatile® FZ 3109, sold by Union Carbide, of formula:

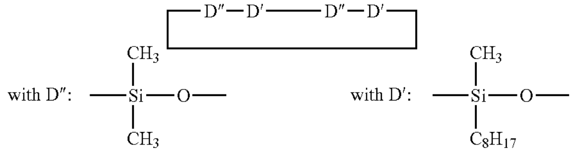

Mention may also be made of mixtures of cyclic polydialkylsiloxanes with silicon-derived organic compounds, such as the mixture of octamethylcyclotetrasiloxane and of tetratrimethylsilylpentaerythritol (50/50) and the mixture of octamethylcyclotetrasiloxane and of 1,1'-oxy(2,2,2',2',3,3'-hexatrimethylsilyloxy)bisneopentane;

(ii) linear volatile polydialkylsiloxanes having from 2 to 9 silicon atoms and exhibiting a viscosity of less than or equal to $5\times10^{-6}$ $m^2/s$ at 25° C. They are, for example, decamethyltetrasiloxane, sold in particular under the name "SH 200" by Toray Silicone. Silicones coming within this category are also described in the article published in Cosmetics and Toiletries, Vol. 91, January 76, pp. 27-32, Todd & Byers, "Volatile Silicone Fluids for Cosmetics". The viscosity of the silicones is measured at 25° C. according to Standard ASTM 445, Appendix C.

Use may also be made of non-volatile polydialkylsiloxanes.

These nonvolatile silicones are chosen more particularly from polydialkylsiloxanes, among which may be mentioned mainly polydimethylsiloxanes possessing trimethylsilyl end groups.

Mention may be made, among these polydialkylsiloxanes, without implied limitation, of the following commercial products:

- Silbione® oils of the 47 and 70 047 series or Mirasil® oils sold by Rhodia, such as, for example, the oil 70 047 V 500 000;
- oils of the Mirasil® series sold by Rhodia;
- oils of the 200 series from Dow Corning, such as DC200 having a viscosity of 60 000 $mm^2/s$;
- Viscasil® oils from General Electric and some oils of the SF series (SF 96, SF 18) from General Electric.

Mention may also be made of polydimethylsiloxanes possessing dimethylsilanol end groups known under the name of dimethiconol (CTFA), such as oils of the 48 series from Rhodia.

The silicones possessing aryl groups include polydiarylsiloxanes, in particular polydiphenylsiloxanes, and polyalkylarylsiloxanes. Mention may be made, by way of example, of the products sold under the following names:

- Silbione® oils of the 70 641 series from Rhodia;
- oils of the Rhodorsil® 70 633 and 763 series from Rhodia;
- the oil Dow Corning 556 Cosmetic Grade Fluid from Dow Corning;
- silicones of the PK series from Bayer, such as the product PK20;
- some oils of the SF series from General Electric, such as SF 1023, SF 1154, SF 1250 and SF 1265.

The liquid fatty esters are preferably liquid esters of saturated or unsaturated and linear or branched $C_1$-$C_{26}$ aliphatic mono- or polyacids and of saturated or unsaturated and linear or branched $C_1$-$C_{26}$ aliphatic mono- or polyalcohols, the total number of carbon atoms in the esters being greater than or equal to 10.

Preferably, for the esters of monoalcohols, at least one of the alcohol or of the acid from which the esters of the invention result is branched.

Mention may be made, among monoesters of monoacids and of monoalcohols, of ethyl palmitate, isopropyl palmitate, alkyl myristates, such as isopropyl myristate or ethyl myristate, isocetyl stearate, 2-ethylhexyl isononanoate, isodecyl neopentanoate or isostearyl neopentanoate.

Use may also be made of esters of $C_4$-$C_{22}$ di- or tricarboxylic acids and of $C_1$-$C_{22}$ alcohols and esters of mono-, di- or tricarboxylic acids and of di-, tri-, tetra- or pentahydroxy $C_4$-$C_{26}$ nonsugar alcohols.

Mention may in particular be made of: diethyl sebacate; diisopropyl sebacate; di(2-ethylhexyl) sebacate; diisopropyl adipate; di(n-propyl) adipate; dioctyl adipate; di(2-ethylhexyl) adipate; diisostearyl adipate; di(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; or diethylene glycol diisononanoate.

The composition can also comprise, as liquid fatty ester, esters and diesters of sugars and of $C_6$-$C_{30}$, preferably $C_{12}$-$C_{22}$, fatty acids. It should be remembered that the term "sugar" is understood to mean oxygen-comprising hydrocarbon compounds which have several alcohol functional groups, with or without aldehyde or ketone functional group, and which comprise at least 4 carbon atoms. These sugars can be monosaccharides, oligosaccharides or polysaccharides.

Mention may be made, as suitable sugars, for example, of sucrose (or saccharose), glucose, galactose, ribose, fucose, maltose, fructose, mannose, arabinose, xylose, lactose and their derivatives, in particular alkyl derivatives, such as methyl derivatives, for example methylglucose.

The esters of sugars and of fatty acids can be chosen in particular from the group consisting of the esters or mixtures of esters of sugars described above and of saturated or unsaturated and linear or branched $C_6$-$C_{30}$, preferably $C_{12}$-$C_{22}$, fatty acids. If they are unsaturated, these compounds can comprise from one to three conjugated or nonconjugated carbon-carbon double bonds.

The esters according to this alternative form can also be chosen from mono-, di-, tri- and tetraesters, polyesters and their mixtures.

These esters can, for example, be oleates, laurates, palmitates, myristates, behenates, cocoates, stearates, linoleates, linolenates, caprates, arachidonates or their mixtures, such as, in particular, mixed oleate/palmitate, oleate/stearate or palmitate/stearate esters.

More particularly, use is made of mono- and diesters and in particular of sucrose, glucose or methylglucose mono- or dioleates, -stearates, -behenates, -oleate/palmitates, -linoleates, -linolenates or -oleate/stearates.

Mention may be made, by way of example, of the product sold under the name Glucate® DO by Amerchol, which is a methylglucose dioleate.

Finally, use may also be made of natural or synthetic esters of mono-, di- or triacids with glycerol.

Mention may be made, among these, of vegetable oils.

Mention may be made, as oils of vegetable origin or synthetic triglycerides which can be used in the composition of the invention as liquid fatty esters, for example, of:

- triglyceride oils of vegetable or synthetic origin, such as liquid triglycerides of fatty acids comprising from 6 to 30 carbon atoms, such as triglycerides of heptanoic or octanoic acids, or also, for example, sunflower, maize, soybean, cucumber, grape seed, sesame, hazelnut, apricot, macadamia, arara, castor or avocado oils, triglycerides of caprylic/capric acids, such as those sold by Stearineries Dubois or those sold under the names Miglyol® 810, 812 and 818 by Dynamit Nobel, jojoba oil or shea butter oil.

Use will preferably be made, as esters according to the invention, of liquid fatty esters resulting from monoalcohols. These fatty alcohols can be unsaturated.

Isopropyl myristate or isopropyl palmitate are particularly preferred.

Preferably, the liquid unsaturated fatty alcohols of the invention comprise from 8 to 30 carbon atoms.

These liquid unsaturated fatty alcohols exhibit, in their structure, at least one double or triple bond. Preferably, the fatty alcohols of the invention have, in their structure, one or more double bonds. When several double bonds are present, they are preferably 2 or 3 in number and they may or may not be conjugated.

These fatty alcohols can be linear or branched.

They can optionally comprise, in their structure, at least one aromatic or nonaromatic ring. Preferably, they are acyclic.

More particularly, the liquid unsaturated fatty alcohols of the invention are chosen from oleyl alcohol, linoleyl alcohol, linolenyl alcohol or undecylenyl alcohol.

Oleyl alcohol is very particularly preferred.

The liquid fatty alcohols can also be saturated branched fatty alcohols. More particularly, the liquid saturated branched fatty alcohols of the invention are chosen from isostearyl alcohol and octyldodecanol.

Preferably, the oil or oils not comprising a carboxylic acid functional group do not comprise oxyalkylene units or glycerol units.

Preferably, the oil or oils not comprising a carboxylic acid functional group of the emulsion according to the invention are non-silicone oils.

According to a preferred embodiment, the oil or oils not comprising a carboxylic acid functional group is or are chosen from liquid petrolatum, polydecenes, liquid esters of fatty acids and/or of fatty alcohols, liquid fatty alcohols and their mixtures and more preferably still from liquid petrolatum, polydecenes, liquid fatty alcohols and their mixtures.

According to the present invention, the emulsion (A) comprises one or more surfactants chosen from oxyalkylenated and/or glycerolated nonionic surfactants having an HLB of less than 8 and preferably of less than or equal to 7.

The term HLB (Hydrophilic-Lipophilic Balance) is well known to a person skilled in the art and denotes the hydrophilic-lipophilic balance of a surfactant.

The HLB of the surfactant or surfactants used according to the invention is the HLB according to Griffin defined in the publication J. Soc. Cosm. Chem., 1954 (Volume 5), pages 249-256.

Nonlimiting examples of surfactants with an HLB of less than are given in particular in the work entitled McCutcheon's Emulsifiers & Detergents, 1998 International Edition, MC Publishing Company, in the chapter HLB Index.

Preferably, the surfactant or surfactants having an HLB of less than 8 are chosen from oxyalkylenated nonionic surfactants.

The term "oxyalkylenated nonionic surfactants" is understood to mean, according to the invention, nonionic surfactants which carry, in their molecule, one or more groups chosen from the following groups: $—CH_2—CH_2—O—$, $—CH_2—CH_2—CH_2—O—$, $—CH_2—CH(CH_3)—O—$ or their mixtures.

The oxyalkylenated nonionic surfactants having an HLB of less than 8 can belong, without implied limitation, to the following families:

oxyethylenated alkylphenols,
ethylene oxide/propylene oxide condensates,
oxyethylenated vegetable oils,
oxyethylenated fatty alcohols,
esters of fatty acids and of polyethyleneglycols,
polyoxyethylenated esters of fatty acids and of sorbitol.

Mention may be made, as commercial compounds, of:

| | | |
|---|---|---|
| Prox-Onic EP 4060-1 | (HLB = 1) | Protex |
| Synperonic PE L101 | (HLB = 1) | ICI |
| Etocas 29 | (HLB = 1.7) | Croda |

-continued

| | | |
|---|---|---|
| Genapol PF 10 | (HLB = 2) | Hoechst |
| Synperonic PE L81 | (HLB = 2) | ICI |
| Prox-Onic EP 1090-1 | (HLB = 3) | Protex |
| Sinnopal DPN2 | (HLB = 3.3) | Henkel |
| Antarox CA 210 | (HLB = 3.5) | Rhône-Poulenc |
| Alkasurf OP11 | (HLB = 3.6) | Rhône-Poulenc |
| Triton X15 | (HLB = 3.6) | Röhm & Haas |
| Alkasurf OP1 | (HLB = 3.6) | Rhône-Poulenc |
| Arlacel 121 | (HLB = 3.8) | ICI |
| Prox-Onic HR or HRH-05 | (HLB = 3.8) | Protex |
| Etocas 5 | (HLB = 3.9) | Hoechst |
| Genapol PF20 | (HLB = 4) | Hoechst |
| Imbentin N/7 A | (HLB = 4) | Kolb |
| Synperonic PE L122 | (HLB = 4) | ICI |
| Ethylan NP1 | (HLB = 4.5) | Harcros |
| Imbentin N/020 | (HLB = 4.5) | Kolb |
| Kotilen O/3/020 | (HLB = 4.5) | Kolb |
| Synperonic PE L31 | (HLB = 4.5) | ICI |
| TO-55-A | (HLB = 4.5) | Hefti |
| Alkasurf NP-1 | (HLB = 4.6) | Rhône-Poulenc |
| Antarox CO 210 | (HLB = 4.6) | Rhône-Poulenc |
| Prox-Onic NP-1 | (HLB = 4.6) | Protex |
| Rhodiasurf NP2 | (HLB = 4.6) | Rhône-Poulenc |
| Soprophor BC2 | (HLB = 4.6) | Rhône-Poulenc |
| Triton N17 | (HLB = 4.6) | Röhm & Haas |
| Akyporox NP15 | (HLB = 4.7) | Chem-Y |
| Texofor M2 | (HLB = 4.8) | Rhône-Poulenc |
| Alkasurf SA2 | (HLB = 4.9) | Rhône-Poulenc |
| Arlacel 989 | (HLB = 4.9) | ICI |
| Brij 72 | (HLB = 4.9) | ICI |
| Brij 92 | (HLB = 4.9) | ICI |
| Brij 93 | (HLB = 4.9) | ICI |
| Prox-Onic SA-1 or 2/02 | (HLB = 4.9) | Protex |
| Simulsol 72 | (HLB = 4.9) | Seppic |
| Simulsol 92 | (HLB = 4.9) | Seppic |
| Volpo S-2 | (HLB = 4.9) | Croda |
| Arlacel 581 | (HLB = 5.0) | ICI |
| Arlacel 582 | (HLB = 5.0) | ICI |
| Genapol O-020 | (HLB = 5.0) | Hoechst |
| Imbentin POA/020 | (HLB = 5.0) | Kolb |
| Mergital Q2 | (HLB = 5.0) | Henkel |
| Imbentin POA/024 | (HLB = 5.5) | ICI |
| Synperonic PE L92 | (HLB = 5.5) | ICI |
| Mergital LM2 | (HLB = 5.8) | Henkel |
| Atlas G-70140 | (HLB = 6) | ICI |
| Imbentin. AG/124S/020 | (HLB = 6) | Kolb |
| Imbentin. L/125/025 | (HLB = 6) | Kolb |
| Simulsol 989 | (HLB = 6) | Seppic |
| Soprophor HR10 | (HLB = 6) | Rhône-Poulenc |
| Kotilen O/1/050 | (HLB = 6.2) | Kolb |
| Croduret 10 | (HLB = 6.3) | Croda |
| Etocas 10 | (HLB = 6.3) | Croda |
| Imbentin OA/030 | (HLB = 6.3) | Kolb |
| Soprophor 208 | (HLB = 6.9) | Rhône-Poulenc |
| Ethylan 172 | (HLB = 7) | Harcros |

More preferably, the said surfactants are chosen from oxyalkylenated nonionic surfactants having an HLB of less than or equal to 5.

According to the invention, the emulsion (A) preferably comprises from 1 to 20% by weight of the said nonionic surfactant or surfactants according to the invention having an HLB of less than 8, more preferably still from 1 to 15% by weight and better still from 2 to 10% by weight, with respect to the total weight of the emulsion (A).

The emulsion (A) can comprise additional surfactants different from the nonionic surfactants according to the invention and in particular surfactants having an HLB of greater than or equal to 8. In this case, the surfactant or surfactants are preferably chosen from nonionic surfactants or from anionic surfactants.

However, according to a specific embodiment, the emulsion (A) does not comprise surfactants other than the surfactants according to the invention having an HLB of less than 8 and chosen from oxyalkylenated and/or glycerolated nonionic surfactants.

According to the present invention, the composition (B) comprises one or more oxidizing agents.

This oxidizing agent can be chosen from oxidizing agents conventionally used for the oxidation dyeing and bleaching of keratinous fibres, among which may be mentioned hydrogen peroxide, urea hydrogen peroxide, alkali metal bromates or ferricyanides, or peroxygenated salts, such as, for example, alkali metal or alkaline earth metal, such as sodium, potassium or magnesium, persulphates, perborates and percarbonates. Use may also be made, as oxidizing agent, of one or more oxidation/reduction enzymes, such as laccases, peroxidazes and 2-electron oxidoreductases (such as uricase), optionally in the presence of their respective donor or cofactor.

The use of hydrogen peroxide is particularly preferred. The latter can advantageously be employed in aqueous solution (aqueous hydrogen peroxide solution), the concentration of which can vary more particularly from 0.1 to 50% by weight, more preferably still from 0.5 to 20% by weight and better still from 1 to 15% by weight, with respect to the total weight of the composition (B).

Depending on the degree of bleaching desired, the oxidizing agent can also comprise one or more compounds preferably chosen from peroxygenated salts.

Preferably, the pH of the composition (B) is less than 7. This pH can be adjusted to the desired value by the use of one or more acidifying agents which can in particular be chosen from those described above.

The composition (B) may or may not comprise one or more oils chosen from oils not comprising a carboxylic acid functional group. When the composition (B) comprises one or more oils, then these oils are as defined for the emulsion (A).

The dyeing and/or bleaching agent according to the invention is such that, after mixing the inverse emulsion (A) and the composition (B), the amount of oil(s) not comprising a carboxylic acid functional group after mixing is at least 20% by weight, preferably between 20.5 and 75% by weight, with respect to the total weight of the mixture.

Preferably, the total amount of oil(s) not comprising a carboxylic acid functional group in the mixture of the inverse emulsion (A) and of the composition (B) represents at least 25% by weight, more particularly is between 25.5 and 75% by weight, more preferably still represents at least 30% by weight and more particularly is between 30.5 and 75% by weight, with respect to the total weight of the mixture of these two compositions.

The composition (B) can additionally comprise one or more surfactants. In this case, the surfactant or surfactants are preferably chosen from nonionic surfactants or from anionic surfactants.

The inverse emulsion (A) and/or the composition (B) according to the present invention can also comprise one or more inorganic thickening agents chosen from organophilic clays, pyrogenic silicas or their mixtures.

The organophilic clay can be chosen from montmorillonite, bentonite, hectorite, attapulgite, sepiolite and their mixtures. The clay is preferably a bentonite or a hectorite.

These clays can be modified with a chemical compound chosen from quaternary ammoniums, tertiary amines, amine acetates, imidazolines, amine soaps, fatty sulphates, alkylarylsulphonates, amine oxides and their mixtures.

Mention may be made, as organophilic clays, of quaternium-18 bentonites, such as those sold under the names Bentone 3, Bentone 38 or Bentone 38V by Rhéox, Tixogel VP by United Catalyst or Claytone 34, Claytone 40 or Claytone XL by Southern Clay; stearalkonium bentonites, such as those sold under the names Bentone 27 by Rheox, Tixogel LG by United Catalyst or Claytone AF or Claytone APA by Southern Clay; or quaternium-18/benzalkonium bentonites, such as those sold under the names Claytone HT or Claytone PS by Southern Clay.

Pyrogenic silicas can be obtained by high temperature hydrolysis of a volatile silicon compound in an oxyhydrogen flame, producing a finely divided silica. This process makes it possible in particular to obtain hydrophilic silicas which exhibit a large number of silanol groups at their surfaces. Such hydrophilic silicas are sold, for example, under the names "Aerosil 130®", "Aerosil 200®", "Aerosil 255®", "Aerosil 300®" or "Aerosil 380®" by Degussa or "Cab-O-Sil HS-5®", "Cab-O-Sil EH-5®", "Cab-O-Sil LM-130®", "Cab-O-Sil MS-55®" or "Cab-O-Sil M-5®" by Cabot.

It is possible to chemically modify the surface of the silica by a chemical reaction for the purpose of decreasing the number of silanol groups. It is possible in particular to substitute silanol groups by hydrophobic groups: a hydrophobic silica is then obtained.

The hydrophobic groups can be:

trimethylsiloxyl groups, which are obtained in particular by treatment of pyrogenic silica in the presence of hexamethyldisilazane. Silicas thus treated are named "Silica silylate" according to the CTFA (6" edition, 1995). They are sold, for example, under the references "Aerosil R812®" by Degussa or "Cab-O-Sil TS-530®" by Cabot.

dimethylsilyloxyl or polydimethylsiloxane groups, which are obtained in particular by treatment of pyrogenic silica in the presence of polydimethylsiloxane or of dimethyldichlorosilane. Silicas thus treated are named "Silica dimethyl silylate" according to the CTFA (6" edition, 1995). They are sold, for example, under the references "Aerosil R972®" or "Aerosil R974®" by Degussa or "Cab-O-Sil TS-610®" or "Cab-O-Sil TS-720®" by Cabot.

The pyrogenic silica preferably exhibits a particle size which can be nanometric to micrometric, for example ranging from approximately 5 to 200 nm.

The preferred inorganic thickening agents are chosen from hectorites, organomodified bentonites and optionally modified pyrogenic silicas.

When it is present, the inorganic thickening agent represents from 1 to 30% by weight, with respect to the weight of the inverse emulsion (A) and/or of the composition (B).

The emulsion (A) and/or the composition (B) according to the present invention can also comprise one or more organic thickening agents.

These thickening agents can be chosen from amides of fatty acids (coconut oil diethanolamide or monoethanolamide, oxyethylenated alkyl ether carboxylic acid monoethanolamide), polymeric thickeners, such as cellulose thickeners (hydroxyethylcellulose, hydroxypropylcellulose, carboxymethylcellulose), guar gum and its derivatives (hydroxypropyl guar), gums of microbial origin (xanthan gum, scleroglucan gum), crosslinked homopolymers of acrylic acid or of acrylamidopropanesulphonic acid and associative polymers (polymers comprising hydrophilic regions and hydrophobic regions having a fatty chain (alkyl or alkenyl chain comprising at least 10 carbon atoms) which are capable, in an aqueous medium, of reversibly associating with one another or with other molecules).

According to a specific embodiment, the organic thickener is chosen from cellulose thickeners (hydroxyethylcellulose, hydroxypropylcellulose, carboxymethylcellulose), guar gum and its derivatives (hydroxypropyl guar), gums of microbial origin (xanthan gum, scleroglucan gum) or crosslinked homopolymers of acrylic acid or of acrylamidopropanesulphonic acid, preferably from cellulose thickeners with in particular hydroxyethylcellulose.

The content of organic thickening agent(s), if they are present, usually varies from 0.01 to 20% by weight, preferably from 0.1 to 5% by weight, with respect to the weight of the inverse emulsion (A) and/or of the composition (B).

The emulsion (A) and/or the composition (B) according to the invention can additionally comprise one or more fatty substances other than the oils not comprising a carboxylic acid functional group defined above, this fatty substance or these fatty substances being devoid of a carboxylic acid functional group, such as, in particular, solid fatty alcohols, such as cetyl alcohol, stearyl alcohol and their mixtures.

Advantageously, the emulsion (A) is provided in the form of a gel or of a cream.

Advantageously, the composition (B) is provided in the form of a solution, of an emulsion or of a gel.

According to one embodiment of the invention, the emulsion (A) additionally comprises one or more oxidation dyes and/or one or more direct dyes.

In this case, the agent according to the invention is advantageously used for the dyeing of keratinous fibres.

When the emulsion (A) comprises solely direct dyes (without oxidation dyes), the agent according to the invention is used for the lightening direct dyeing of keratinous fibres.

The oxidation dyes which can be used in the present invention are generally chosen from oxidation bases, optionally in combination with one or more couplers.

The oxidation bases can be chosen in particular from para-phenylenediamines, bisphenylalkylenediamines, para-aminophenols, ortho-aminophenols, heterocyclic bases and their addition salts.

Mention may be made, among para-phenylenediamines, by way of example, of para-phenylenediamine, para-toluoylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-(β-hydroxyethyl)-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl, (β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-(β-hydroxyethyloxy)-para-phenylenediamine, 2-(β-acetylaminoethyloxy)-para-phenylenediamine, N-(β-methoxyethyl)-para-phenylenediamine, 4-aminophenylpyrrolidine, 2-thienyl-para-phenylenediamine, 2-(β-hydroxyethylamino)-5-aminotoluene, 3-hydroxy-1-(4'-aminophenyl)pyrrolidine and their addition salts with an acid.

Among the para-phenylenediamines mentioned above, para-phenylenediamine, para-toluoylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-(β- acetylaminoethyloxy)-para-phenylenediamine and their addition salts with an acid are particularly preferred.

Mention may be made, among bisphenylalkylenediamines, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylamino-phenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane and their addition salts.

Mention may be made, among para-aminophenols, by way of example, of para-aminophenol, 4-amino-3-methylphenol, 4-amino-3-fluorophenol, 4-amino-3-chlorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-2-(aminomethyl)phenol, 4-amino-2-[(β-hydroxyethyl)aminomethyl]-phenol, 4-amino-2-fluorophenol and their addition salts with an acid.

Mention may be made, among ortho-aminophenols, by way of example, of 2-aminophenol, 2-amino-5-methylphenol, 2-amino-6-methylphenol, 5-acetamido-2-aminophenol and their addition salts.

Mention may be made, among heterocyclic bases, by way of example, of pyridine derivatives, pyrimidine derivatives and pyrazole derivatives.

Mention may be made, among pyridine derivatives, of the compounds described, for example, in Patents GB 1 026 978 and GB 1 153 196, such as 2,5-diaminopyridine, 2-[(4-methoxyphenyl)amino]-3-aminopyridine, 3,4-diaminopyridine and their addition salts.

Other pyridine oxidation bases of use in the present invention are the 3-aminopyrazolo[1,5-a]pyridine oxidation bases or their addition salts described, for example, in Patent Application FR 2 801 308. Mention may be made, by way of example, of pyrazolo[1,5-a]pyridin-3-ylamine; 2-(acetylamino)pyrazolo[1,5-a]pyridin-3-ylamine; 2-(morpholin-4-yl)pyrazolo[1,5-a]pyridin-3-ylamine; 3-aminopyrazolo[1,5-a]pyridine-2-carboxylic acid; 2-methoxypyrazolo[1,5-a]pyridin-3-ylamine; (3-aminopyrazolo[1,5-a]-pyridin-7-yl)methanol; 2-(3-aminopyrazolo[1,5-a]pyridin-5-yl)ethanol; 2-(3-aminopyrazolo[1,5-a]pyridin-7-yl)ethanol; (3-aminopyrazolo[1,5-a]pyridin-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-(morpholin-4-yl)pyrazolo[1,5-a]pyridin-3-ylamine; pyrazolo[1,5-a]pyridine-3,5-diamine; 5-(morpholin-4-yl)pyrazolo[1,5-a]pyridin-3-ylamine; 2-[(3-aminopyrazolo[1,5-a]pyridin-5-yl)(2-hydroxyethyl)amino]ethanol; 2-[(3-aminopyrazolo[1,5-a]pyridin-7-yl)(2-hydroxyethyl)amino]ethanol; 3-aminopyrazolo[1,5-a]pyridin-5-ol; 3-aminopyrazolo[1,5-a]pyridin-4-ol; 3-aminopyrazolo[1,5-a]pyridin-6-ol; 3-aminopyrazolo[1,5-a]pyridin-7-ol; and their addition salts.

Mention may be made, among pyrimidine derivatives, of the compounds described, for example, in Patents DE 2 359 399; JP 88-169571; JP 05-63124; EP 0 770 375 or Patent Application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Mention may be made, among pyrazole derivatives, of the compounds described in Patents DE 3 843 892 and DE 4 133 957 and Patent Applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-(tert-butyl)-1-methyl-pyrazole, 4,5-diamino-1-(tert-butyl)-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-(hydroxymethyl)pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-(methylamino)pyrazole, 3,5-diamino-4-(β-hydroxyethyl)amino-1-methylpyrazole and their addition salts. Use may also be made of 4,5-diamino-1-(β-methoxyethyl)pyrazole.

Use will preferably be made of a 4,5-diaminopyrazole and more preferably still of 4,5-diamino-1-(β-hydroxyethyl)pyrazole and/or one of its salts.

Mention may also be made, as pyrazole derivatives, of diamino-N,N-dihydropyrazolopyrazolones, in particular those described in Application FR-A-2 886 136, such as the following compounds and their addition salts: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-[3-(dimethylamino)pyrrolidin-1-yl]-1,2-diethyl-1,2-dihydropyrazol-3-one or 2,3-diamino-6-hydroxy-6,7-dihydro-1H,5H-pyrazolo[1,2-a]pyrazol-1-one.

It will be preferable to use 2,3-diamino-6,7-dihydro-1H,5H-pyrazolo[1,2-a]pyrazol-1-one and/or one of its salts.

Use will preferably be made, as heterocyclic bases, of 4,5-diamino-1-(β-hydroxyethyl)pyrazole and/or 2,3-diamino-6,7-dihydro-1H,5H-pyrazolo[1,2-a]pyrazol-1-one and/or one of their salts.

The couplers which can be used in the present invention can be chosen from those conventionally used for dyeing keratinous fibres.

Mention may in particular be made, among these couplers, of meta-phenylenediamines, meta-aminophenols, meta-diphenols, naphthalene couplers or heterocyclic couplers and their addition salts.

Mention may be made, by way of example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 6-methylpyrazolo[1,5-a]benzimidazole, their addition salts with an acid and their mixtures.

Generally, the addition salts of the oxidation bases and couplers which can be used in the context of the invention are chosen in particular from the addition salts with an acid, such as hydrochlorides, hydrobromides, sulphates, citrates, succinates, tartrates, lactates, tosylates, benzenesulphonates, phosphates and acetates.

The oxidation base or bases can each advantageously represent from 0.0001 to 10% by weight, with respect to the total weight of the emulsion (A), and preferably from 0.005 to 5% by weight, with respect to the total weight of this emulsion.

The coupler or couplers, if they are present, can each advantageously represent from 0.0001 to 10% by weight, with respect to the total weight of the emulsion (A), and preferably from 0.005 to 5% by weight, with respect to the total weight of this emulsion.

The direct dyes capable of being employed in the emulsion (A) are more particularly chosen from ionic or nonionic entities, preferably cationic or nonionic entities.

Mention may be made, as examples of suitable direct dyes, of azo, methine, carbonyl, azine, nitro(hetero)aryl or tri(hetero)arylmethane direct dyes, porphyrins, phthalocyanines and natural direct dyes, alone or as mixtures.

More particularly, azo dyes comprise an —N═N— functional group, the two nitrogen atoms of which are not simultaneously participants in a ring. However, it is not out of the question for one of the two nitrogen atoms of the —N═N— sequence to be a participant in a ring.

Dyes of the family of the methines are more particularly compounds comprising at least one sequence chosen from >C═C< and —N═C<, the two atoms of which are not simultaneously participants in a ring. However, it is specified that one of the nitrogen or carbon atoms of the sequences can be a participant in a ring. More particularly, the dyes of this family result from compounds of the following types: methine, azomethine, mono- and diarylmethane, indoamines (or diphenylamines), indophenols, indoanilines, carbocyanines, azacarbocyanines and their isomers, diazacarbocyanines and their isomers, tetraazacarbocyanines or hemicyanines.

As regards dyes of the family of the carbonyls, mention may be made, for example, of dyes chosen from acridone, benzoquinone, anthraquinone, naphthoquinone, benzanthrone, anthranthrone, pyranthrone, pyrazolanthrone, pyrimidinoanthrone, flavanthrone, indanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole or coumarin dyes.

As regards dyes of the family of the cyclic azines, mention may in particular be made of azine, xanthene, thioxanthene, fluorindine, acridine, (di)oxazine, (di)thiazine or pyronine dyes.

The nitro(hetero)aromatic dyes are more particularly nitrobenzene or nitropyridine direct dyes.

As regards the dyes of porphyrin or phthalocyanine type, use may be made of cationic or noncationic compounds optionally comprising one or more metals or metal ions, such as, for example, alkali and alkaline earth metals, zinc and silicon.

Mention may be made, as examples of direct dyes which are particularly suitable, of nitrobenzene dyes, azo, azomethine or methine direct dyes, azacarbocyanines, such as tetraazacarbocyanines (tetraazapentamethines), quinone and in particular anthraquinone, naphthoquinone or benzoquinone direct dyes, azine, xanthene, triarylmethane, indoamine or indigoid direct dyes, phthalocyanines, porphyrins and natural direct dyes, alone or as mixtures.

These dyes can be monochromophoric dyes (that is to say, comprising only a single dye) or polychromophoric dyes, preferably di- or trichromophoric dyes, it being possible for the chromophores to be identical or different and from the same or a different chemical family. It should be noted that a polychromophoric dye comprises several radicals, each resulting from a molecule which absorbs in the visible region between 400 and 800 nm. Furthermore, this absorbance of the dye requires neither preoxidation of the latter nor combination with other chemical entity(ies).

In the case of polychromophoric dyes, the chromophores are connected to one another by means of at least one connecting arm, which may or may not be cationic.

Preferably, the connecting arm is a linear, branched or cyclic $C_1$-$C_{20}$ alkyl chain which is optionally interrupted by at least one heteroatom (such as nitrogen or oxygen) and/or by at least one group comprising it (CO, $SO_2$), which is optionally interrupted by at least one heterocycle which may or may not be fused with a phenyl nucleus and which comprises at least one quaternized nitrogen atom participating in the said cycle and optionally at least one other heteroatom (such as oxygen, nitrogen or sulphur), which is optionally interrupted by at least one substituted or unsubstituted phenyl or naphthyl group and which is optionally interrupted by at least one quaternary ammonium group substituted by two optionally substituted $C_1$-$C_{15}$ alkyl groups, the connecting arm not comprising a nitro, nitroso or peroxo group.

If the heterocycles or aromatic nuclei are substituted, they are substituted, for example, by one or more $C_1$-$C_8$ alkyl radicals optionally substituted by a hydroxyl group, a $C_1$-$C_2$ alkoxy group, a $C_2$-$C_4$ hydroxyalkoxy group, an acetylamino group, an amino group substituted by one or two $C_1$-$C_4$ alkyl radicals which optionally carry at least one hydroxyl group or it being possible for the two radicals to form, with the nitrogen atom to which they are attached, a 5- or 6-membered heterocycle optionally comprising another heteroatom identical to or different from nitrogen; a halogen atom; a hydroxyl group; a $C_1$-$C_2$ alkoxy radical; a $C_2$-$C_4$ hydroxyalkoxy radical; an amino radical; or an amino radical substituted by one or two identical or different $C_1$-$C_4$ alkyl radicals which optionally carry at least one hydroxyl group.

Mention may be made, among the benzene direct dyes which can be used according to the invention, without implied limitation, of the following compounds:

1,4-diamino-2-nitrobenzene
1-amino-2-nitro-4-(β-hydroxyethylamino)benzene
1-amino-2-nitro-4-[bis(β-hydroxyethyl)amino]benzene
1,4-bis(β-hydroxyethylamino)-2-nitrobenzene
1-(β-hydroxyethylamino)-2-nitro-4-[bis(β-hydroxyethyl)amino]benzene
1-(β-hydroxyethylamino)-2-nitro-4-aminobenzene
1-(β-hydroxyethylamino)-2-nitro-4-[(ethyl)(β-hydroxyethyl)amino]benzene
1-amino-3-methyl-4-(β-hydroxyethylamino)-6-nitrobenzene
1-amino-2-nitro-4-(β-hydroxyethylamino)-5-chlorobenzene
1,2-diamino-4-nitrobenzene
1-amino-2-(β-hydroxyethylamino)-5-nitrobenzene
1,2-bis(β-hydroxyethylamino)-4-nitrobenzene
1-amino-2-[tris(hydroxymethyl)methylamino]-5-nitrobenzene 1-hydroxy-2-amino-5-nitrobenzene 1-hydroxy-2-amino-4-nitrobenzene 1-hydroxy-3-nitro-4-aminobenzene 1-hydroxy-2-amino-4,6-dinitrobenzene 1-(β-hydroxyethyloxy)-2-(β-hydroxyethylamino)-5-nitrobenzene 1-methoxy-2-(β-hydroxyethylamino)-5-nitrobenzene 1-(β-hydroxyethyloxy)-3-methylamino-4-nitrobenzene 1-(β,γ-dihydroxypropyloxy)-3-methylamino-4-nitrobenzene 1-(β-hydroxyethylamino)-4-(β,γ-dihydroxypropyloxy)-2-nitrobenzene 1-(β,γ-dihydroxypropylamino)-4-trifluoromethyl-2-nitrobenzene 1-(β-hydroxyethylamino)-4-trifluoromethyl-2-nitrobenzene 1-(β-hydroxyethylamino)-3-methyl-2-nitrobenzene 1-(β-aminoethylamino)-5-methoxy-2-nitrobenzene 1-hydroxy-2-chloro-6-ethylamino-4-nitrobenzene 1-hydroxy-2-chloro-6-amino-4-nitrobenzene 1-hydroxy-6[bis(β-hydroxyethyl)amino]-3-nitrobenzene 1-(β-hydroxyethylamino)-2-nitrobenzene 1-hydroxy-4-(β-hydroxyethylamino)-3-nitrobenzene.

Mention may be made, among the azo, azomethine, methine or tetraazapentamethine direct dyes which can be used according to the invention, of the cationic dyes described in Patent Applications WO 95/15144, WO 95/01772 and EP 714 954; FR 2 189 006, FR 2 285 851, FR 2 140 205, EP 1 378 544 and EP 1 674 073.

Thus, mention may very particularly be made of the following dyes of formulae (I) to (IV) below and preferably of the compounds of following formulae (I) and (III):

(I)

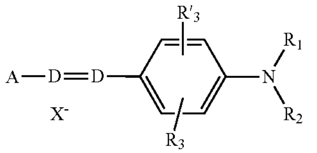

in which:

D represents a nitrogen atom or the —CH group, $R_1$ and $R_2$, which are identical or different, represent a hydrogen atom; a $C_1$-$C_4$ alkyl radical which can be substituted by a —CN, —OH or —$NH_2$ radical or form, with a carbon atom of the benzene ring, an optionally oxygen-comprising or nitrogen-comprising heterocycle which can be substituted by one or more $C_1$-$C_4$ alkyl radicals; or a 4'-aminophenyl radical, $R_3$ and $R'_3$, which are identical or different, represent a hydrogen atom, a halogen atom chosen from chlorine, bromine, iodine and fluorine, a cyano radical, a $C_1$-$C_4$ alkyl radical, a $C_1$-$C_4$ alkoxy radical or an acetyloxy radical, X" represents an anion, preferably chosen from chloride, methyl sulphate and acetate, A represents a group chosen from the following structures A1 to A18, preferably A1, A4, A7, A13 and A18:

$A_1$

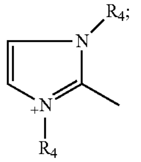

$A_2$

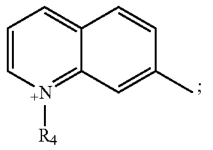

$A_3$

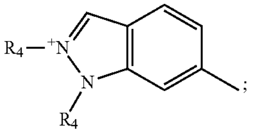

$A_4$

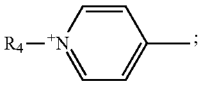

$A_5$

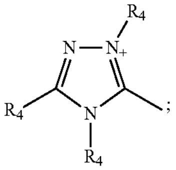

$A_6$

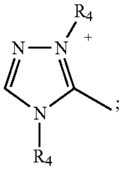

$A_7$

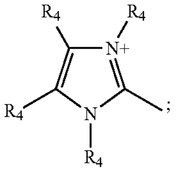

$A_8$

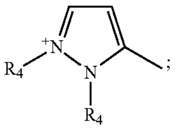

$A_9$

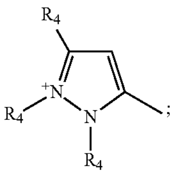

-continued

A10

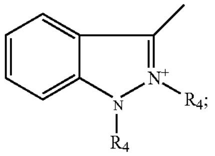

A11

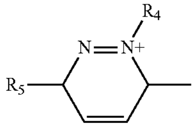
;

A12

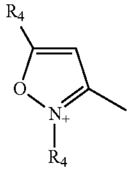
;

A13

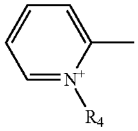
;

A14

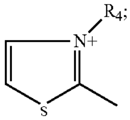

A15

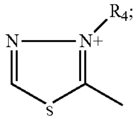

A16

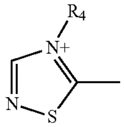
;

A17

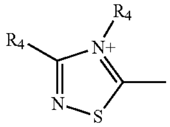
;

A18

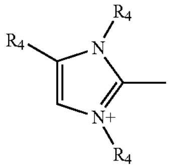
;

in which $R_4$ represents a $C_1$-$C_4$ alkyl radical which can be substituted by a hydroxyl radical and $R_5$ represents a $C_1$-$C_4$ alkoxy radical;

(II)

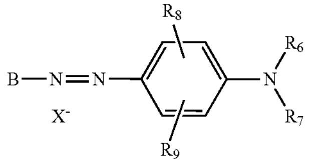

in which:

$R_6$ represents a hydrogen atom or a $C_1$-$C_4$ alkyl radical, $R_7$ represents a hydrogen atom, an alkyl radical which can be substituted by a —CN radical or by an amino group, or a 4'-aminophenyl radical, or forms, with $R_6$, an optionally oxygen-comprising and/or nitrogen-comprising heterocycle which can be substituted by a $C_1$-$C_4$ alkyl radical, $R_8$ and $R_9$, which are identical or different, represent a hydrogen atom, a halogen atom, such as bromine, chlorine, iodine or fluorine, a $C_1$-$C_4$ alkyl radical, a $C_1$-$C_4$ alkoxy radical or a —CN radical, $X^-$ represents an anion, preferably chosen from chloride, methyl sulphate and acetate, B represents a group chosen from the following structures B1 to B6:

B1

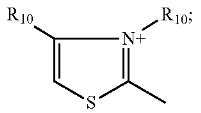

B2

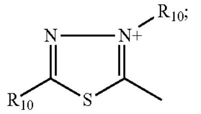

B3

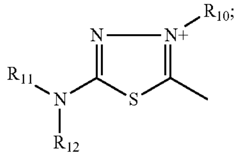

B4

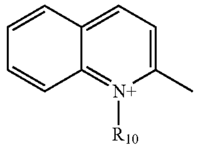

B5

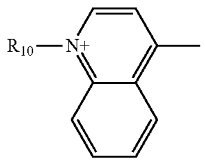

B6

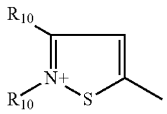

in which $R_{10}$ represents a $C_1$-$C_4$ alkyl radical and $R_{11}$ and $R_{12}$, which are identical or different, represent a hydrogen atom or a $C_1$-$C_4$ alkyl radical;

(III)

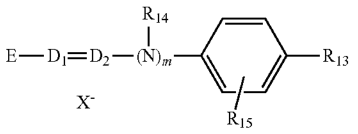

(III')

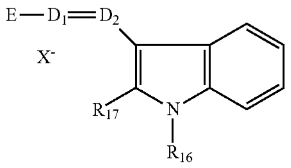

in which:

$R_{13}$ represents a hydrogen atom, a $C_1$-$C_4$ alkoxy radical or a halogen atom, such as bromine, chlorine, iodine or fluorine, $R_{14}$ represents a hydrogen atom or a $C_1$-$C_4$ alkyl radical or forms, with a carbon atom of the benzene ring, a heterocycle which may comprise oxygen and/or may be substituted by one or more $C_1$-$C_4$ alkyl groups, $R_{15}$ represents a hydrogen atom or a halogen atom, such as bromine, chlorine, iodine or fluorine, $R_{16}$ and $R_{17}$, which are identical or different, represent a hydrogen atom or a $C_1$-$C_4$ alkyl radical, $D_1$ and $D_2$, which are identical or different, represent a nitrogen atom or the —CH group, m=0 or 1, preferably 1, it being understood that, when $R_{13}$ represents an unsubstituted amino group, then $D_1$ and $D_2$ simultaneously represent a —CH group and m=0, $X^-$ represents an anion, preferably chosen from chloride, methyl sulphate and acetate, E represents a group chosen from the following structures E1 to E8, more particularly E1, E2 and E7:

E1

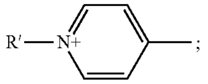

E2

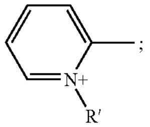

E3

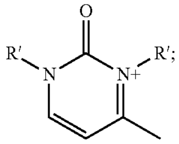

E4

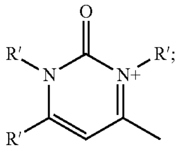

-continued

E5

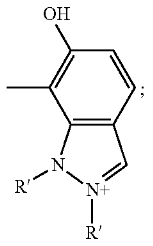

E6

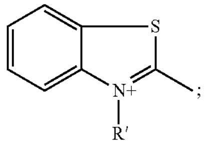

E7

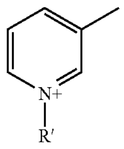

et

E8

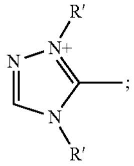

in which R' represents a $C_1$-$C_4$ alkyl radical;

when m=0 and when $D_1$ represents a nitrogen atom, then E can also denote a group with the following structure E9:

E9

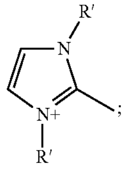

in which R' represents a $C_1$-$C_4$ alkyl radical;

G-N═N-J (IV)

in which:

the symbol G represents a group chosen from the following structures $G_1$ to $G_3$:

$G_1$

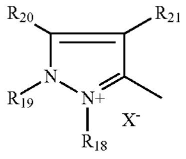

-continued

G2

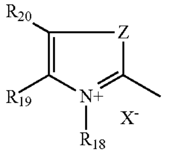

G3

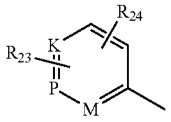

in which structures $G_1$ to $G_3$:

$R_{18}$ denotes a $C_1$-$C_4$ alkyl radical or a phenyl radical which can be substituted by a $C_1$-$C_4$ alkyl radical or a halogen atom chosen from chlorine, bromine, iodine and fluorine;

$R_{19}$ denotes a $C_1$-$C_4$ alkyl radical or a phenyl radical;

$R_{20}$ and $R_{21}$, which are identical or different, represent a $C_1$-$C_4$ alkyl radical or a phenyl radical or together form, in $G_1$, a benzene ring substituted by one or more $C_1$-$C_4$ alkyl, $C_1$-$C_4$ alkoxy or $NO_2$ radicals or together form, in $G_2$, a benzene ring optionally substituted by one or more $C_1$-$C_4$ alkyl, $C_1$-$C_4$ alkoxy or $NO_2$ radicals;

$R_{20}$ can additionally denote a hydrogen atom;

Z denotes an oxygen or sulphur atom or an —$NR_{19}$ group;

M represents a —CH group, a —CR group (R denoting $C_1$-$C_4$ alkyl) or an —$NR_{22}(X^-)$, group;

K represents a —CH group, a —CR group (R denoting $C_1$-$C_4$ alkyl) or an —$NR_{22}(X^-)_r$ group;

P represents a —CH group, a —CR group (R denoting $C_1$-$C_4$ alkyl) or an —$NR_{22}(X^-)_r$ group; r denotes zero or 1;

$R_{22}$ represents an $O^-$ atom, a $C_1$-$C_4$ alkoxy radical or a $C_1$-$C_4$ alkyl radical;

$R_{23}$ and $R_{24}$, which are identical or different, represent a hydrogen atom, a halogen atom chosen from chlorine, bromine, iodine and fluorine, a $C_1$-$C_4$ alkyl radical, a $C_1$-$C_4$ alkoxy radical or an —$NO_2$ radical;

$X^-$ represents an anion, preferably chosen from chloride, iodide, methyl sulphate, ethyl sulphate, acetate and perchlorate;

with the proviso that, if $R_{22}$ denotes $O^-$, then r denotes zero;

if K or P or M denote —N—($C_1$-$C_4$ alkyl) $X^-$, then $R_{23}$ or $R_{24}$ is preferably other than a hydrogen atom;

if K denotes —$NR_{22}(X^-)_r$, then M=P=—CH or —CR;

if M denotes —$NR_{22}(X^-)_r$, then K=P=—CH or —CR;

if P denotes —$NR_{22}(X^-)_r$, then K=M and denotes —CH or —CR;

if Z denotes a sulphur atom with $R_{21}$ denoting $C_1$-$C_4$ alkyl, then $R_{20}$ is other than a hydrogen atom;

if Z denotes —$NR_{22}$ with $R_{19}$ denoting $C_1$-$C_4$ alkyl, then at least one of the $R_{18}$, $R_{20}$ or $R_{21}$ radicals of the group with the structure $G_2$ is other than a $C_1$-$C_4$ alkyl radical;

the symbol J represents:

(a) a group with the following structure $J_1$:

J1

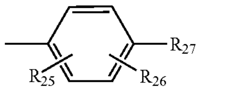

in which structure $J_1$:

$R_{25}$ represents a hydrogen atom, a halogen atom chosen from chlorine, bromine, iodine and fluorine or a $C_1$-$C_4$ alkyl, $C_1$-$C_4$ alkoxy, —OH, —$NO_2$, —$NHR_{28}$, —$NR_{29}R_{30}$ or —NHCO($C_1$-$C_4$ alkyl) radical or forms, with $R_{26}$, a 5- or 6-membered ring which may or may not comprise one or more heteroatoms chosen from nitrogen, oxygen or sulphur;

$R_{26}$ represents a hydrogen atom, a halogen atom chosen from chlorine, bromine, iodine and fluorine, a $C_1$-$C_4$ alkyl radical or a $C_1$-$C_4$ alkoxy radical, or forms, with $R_{27}$ or $R_{28}$, a 5- or 6-membered ring which may or may not comprise one or more heteroatoms chosen from nitrogen, oxygen or sulphur;

$R_{27}$ represents a hydrogen atom, an —OH radical, an —$NHR_{28}$ radical or an —$NR_{29}R_{30}$ radical;

$R_{28}$ represents a hydrogen atom, a $C_1$-$C_4$ alkyl radical, a $C_1$-$C_4$ monohydroxyalkyl radical, a $C_2$-$C_4$ polyhydroxyalkyl radical or a phenyl radical;

$R_{29}$ and $R_{30}$, which are identical or different, represent a $C_1$-$C_4$ alkyl radical, a $C_1$-$C_4$ monohydroxyalkyl radical or a $C_2$-$C_4$ polyhydroxyalkyl radical;

(b) a 5- or 6-membered nitrogenous heterocyclic group which is capable of including other heteroatoms and/or carbonyl groups and which can be substituted by one or more $C_1$-$C_4$ alkyl, amino or phenyl radicals, and in particular a group with the following structure $J_2$:

J2

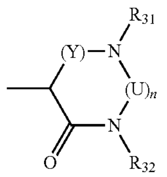

in which structure $J_2$:

$R_{31}$ and $R_{32}$, which are identical or different, represent a hydrogen atom, a $C_1$-$C_4$ alkyl radical or a phenyl radical;

Y denotes the —CO— radical or the

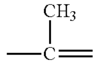

radical;

n=0 or 1, with, when n denotes 1, U denoting the —CO— radical.

In the structures of the dyes (I) to (IV) defined above, the $C_1$-$C_4$ alkyl or alkoxy group preferably denotes methyl, ethyl, butyl, methoxy or ethoxy.

Preference is given, among the compounds of formulae (I) and (III), to the following compounds:

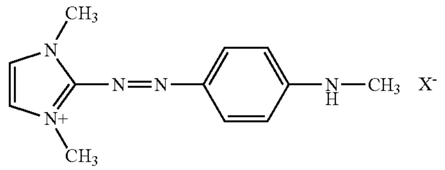

-continued

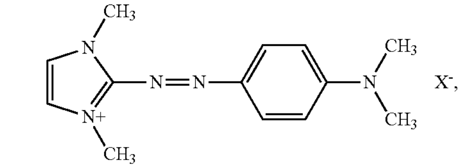

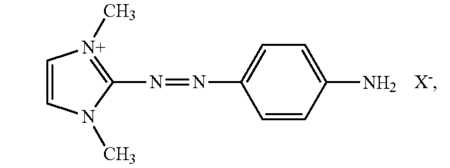

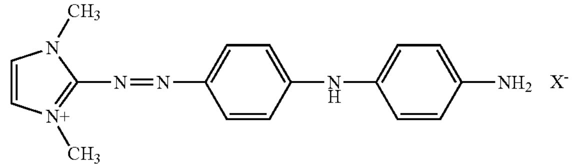

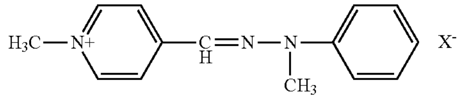

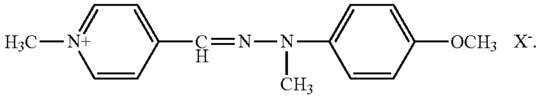

Mention may also be made, among azo direct dyes, of the following dyes described in the Colour Index International, 3rd edition:

Disperse Red 17
Basic Red 22
Basic Red 76
Basic Yellow 57
Basic Brown 16
Basic Brown 17
Disperse Black 9.

Mention may also be made of 1-(4'-aminodiphenylazo)-2-methyl-4-[bis(β-hydroxyethyl)amino]benzene.

Mention may be made, among quinone direct dyes, of the following dyes:

Disperse Red 15
Solvent Violet 13
Disperse Violet 1
Disperse Violet 4
Disperse Blue 1
Disperse Violet 8
Disperse Blue 3
Disperse Red 11
Disperse Blue 7
Basic Blue 22
Disperse Violet 15
Basic Blue 99 and the following compounds:

1-(N-methylmorpholiniopropylamino)-4-hydroxyanthraquinone
1-aminopropylamino-4-(methylamino)anthraquinone
1-(aminopropylamino)anthraquinone
5-(β-hydroxyethyl)-1,4-diaminoanthraquinone
2-(aminoethylamino)anthraquinone
1,4-bis(β,γ-dihydroxypropylamino)anthraquinone.

Mention may be made, among azine dyes, of the following compounds:

Basic Blue 17
Basic Red 2.

Mention may be made, among triarylmethane dyes which can be used according to the invention, of the following compounds:

Basic Green 1
Basic Violet 3
Basic Violet 14
Basic Blue 7
Basic Blue 26.

Mention may be made, among indoamine dyes which can be used according to the invention, of the following compounds:

2-β-hydroxyethylamino-5-[bis(β-4'-hydroxyethyl)amino]aniline-1,4-benzoquinone
2-β-hydroxyethylamino-5-(2'-methoxy-4'-amino)anilino-1,4-benzoquinone
3-N(2'-chloro-4'-hydroxy)phenyl-acetylamino-6-methoxy-1,4-benzoquinone imine
3-N(3'-chloro-4'-methylamino)phenyl-ureido-6-methyl-1,4-benzoquinone imine
3-[4'-N-(ethyl,carbamylmethyl)amino]phenyl-ureido-6-methyl-1,4-benzoquinone imine.

Mention may be made, among dyes of tetraazapentamethine type which can be used according to the invention, of the following compounds which appear in the table below, X being defined as above:

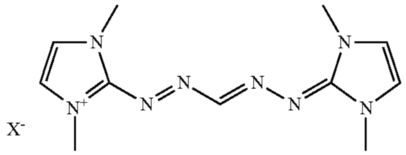

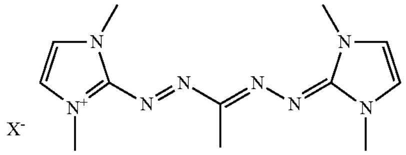

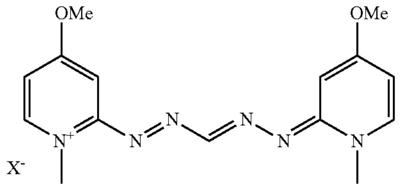

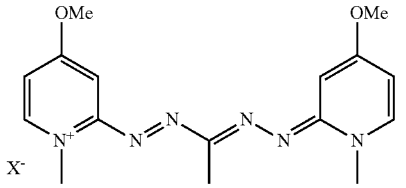

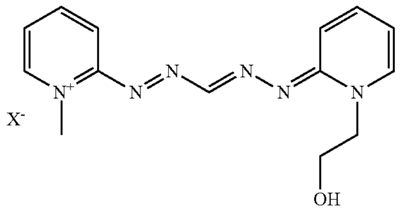

-continued

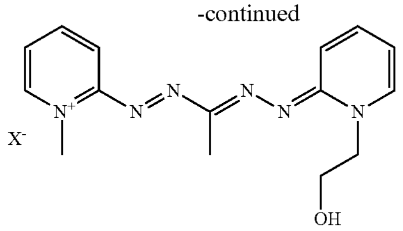

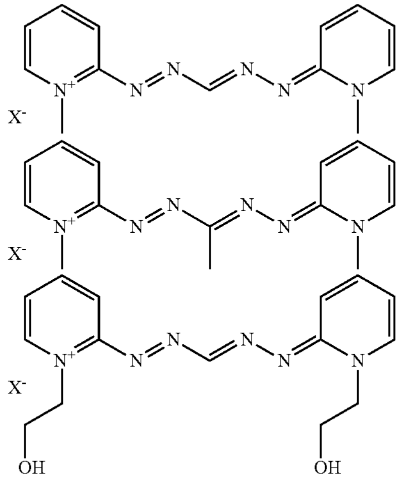

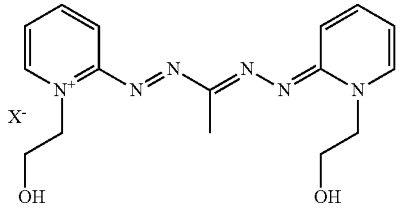

$X^-$ represents an anion, preferably chosen from chloride, iodide, methyl sulphate, ethyl sulphate, acetate and perchlorate.

Mention may more particularly be made, among polychromophoric dyes, of symmetrical or asymmetrical di- or trichromophoric azo and/or azomethine (hydrazone) dyes comprising, on the one hand, at least one optionally fused 5- or 6-membered aromatic heterocycle comprising at least one quaternized nitrogen atom participating in the said heterocycle and optionally at least one other heteroatom (such as nitrogen, sulphur or oxygen) and, on the other hand, at least one optionally substituted phenyl or naphthyl group optionally carrying at least one OR group with R representing a hydrogen atom, an optionally substituted $C_1$-$C_6$ alkyl radical or an optionally substituted phenyl ring or at least one $N(R')_2$ group with R', which are identical or different, representing a hydrogen atom, an optionally substituted $C_1$-$C_6$ alkyl radical or an optionally substituted phenyl ring, it being possible for the R' radicals to form, with the nitrogen atom to which they are bonded, a saturated 5- or 6-membered heterocycle, or alternatively either and/or both R' radicals can form, each with the carbon atom of the aromatic ring in the ortho position with respect to the nitrogen atom, a saturated 5- or 6-membered heterocycle.

Mention may preferably be made, as cationic aromatic heterocycle, of 5- or 6-membered rings comprising from 1 to 3 nitrogen atoms, preferably 1 or 2 nitrogen atoms, one being quaternized, the said heterocycle furthermore optionally being fused with a benzene ring. It should likewise be noted that the heterocycle can optionally comprise another heteroatom other than nitrogen, such as sulphur or oxygen.

If the heterocycles or phenyl or naphthyl groups are substituted, they are substituted, for example, by one or more $C_1$-$C_8$ alkyl radicals optionally substituted by a hydroxyl group, a $C_1$-$C_2$ alkoxy group, a $C_2$-$C_4$ hydroxyalkoxy group, an acetylamino group, an amino group substituted by one or two $C_1$-$C_4$ alkyl radicals which optionally carry at least one hydroxyl group or it being possible for the two radicals to form, with the nitrogen atom to which they are attached, a 5- or 6-membered heterocycle optionally comprising another heteroatom identical to or different from nitrogen; a halogen atom; a hydroxyl group; a $C_1$-$C_2$ alkoxy radical; a $C_2$-$C_4$ hydroxyalkoxy radical; an amino radical; or an amino radical substituted by one or two identical or different $C_1$-$C_4$ alkyl radicals which optionally carry at least one hydroxyl group.

These polychromophores are connected to one another by means of at least one connecting arm optionally comprising at least one quaternized nitrogen atom which may or may not participate in a saturated or unsaturated and optionally aromatic heterocycle.

Preferably, the connecting arm is a linear, branched or cyclic $C_1$-$C_{20}$ alkyl chain which is optionally interrupted by at least one heteroatom (such as nitrogen or oxygen) and/or by at least one group comprising it (CO, $SO_2$), which is optionally interrupted by at least one heterocycle which may or may not be fused with a phenyl nucleus and which comprises at least one quaternized nitrogen atom participating in the said cycle and optionally at least one other heteroatom (such as oxygen, nitrogen or sulphur), which is optionally interrupted by at least one substituted or unsubstituted phenyl or naphthyl group and which is optionally interrupted by at least one quaternary ammonium group substituted by two optionally substituted $C_1$-$C_{15}$ alkyl groups, the connecting arm not comprising a nitro, nitroso or peroxo group.

The connection between the connecting arm and each chromophore is generally made by means of a heteroatom substituting the phenyl or naphthyl nucleus or by means of the quaternized nitrogen atom of the cationic heterocycle.

The dye can comprise identical or different chromophores.

Reference may in particular be made, as examples of such dyes, to Patent Applications EP 1 637 566, EP 1 619 221, EP 1 634 926, EP 1 619 220, EP 1 672 033, EP 1 671 954, EP 1 671 955, EP 1 679 312, EP 1 671 951, EP 167 952, EP 167 971, WO 06/063866, WO 06/063867, WO 06/063868, WO 06/063869, EP 1 408 919, EP 1 377 264, EP 1 377 262, EP 1 377 261, EP 1 377 263, EP 1 399 425, EP 1 399 117, EP 1 416 909, EP 1 399 116 and EP 1 671 560.

Use may also be made of cationic direct dyes mentioned in Applications EP 1 006 153, which describes dyes comprising two chromophores of anthraquinone type connected by means of a cationic connecting arm; EP 1 433 472, EP 1 433 474, EP 1 433 471 and EP 1 433 473, which describe identical or different dichromophoric dyes connected via a cationic or noncationic connecting arm, and EP 6 291 333, which describes in particular dyes comprising three chromophores, one of them being an anthraquinone chromophore to which two chromophores of azo or diazacarbocyanine type or one of its isomers are connected.

Mention may be made, among natural direct dyes which can be used according to the invention, of lawsone, juglone, alizarin, purpurin, carminic acid, kermesic acid, purpurogallin, protocatechualdehyde, indigo, isatin, curcumin, spinulosin, apigenidin, orceins, brazilin, brazilein, haematein or haematoxylin. Use may also be made of extracts or decoctions comprising these natural dyes and in particular cataplasms or henna-based extracts.

When they are present, the direct dye or dyes advantageously represent from 0.0001 to 10% by weight of the total weight of the emulsion (A) and preferably from 0.005 to 5% by weight.

According to another embodiment of the invention, the emulsion (A) and the composition (B) do not comprise a direct dye or an oxidation dye (bases and couplers) or else, if they are present, their total content does not exceed 0.005% by weight, with respect to the total weight of each composition.

In this embodiment, the agent according to the invention is advantageously used for the bleaching of keratinous fibres.

In this embodiment, the emulsion (A) can advantageously comprise one or more solid or pasty and preferably pulverulent adjuvants. The adjuvants can then be chosen from clays, salts other than ammonium salts, natural or synthetic thickeners, optionally modified starch, glass beads, silica, nylon, alumina, titanium dioxide, zeolites, poly(methyl methacrylate) (PMMA), chitosan, maltodextrin, cyclodextrin, mono- or disaccharides, such as glucose, sucrose, sorbitol or fructose, zinc oxide, zirconium oxide, silica beads, talc, borosilicates, in particular calcium borosilicate, polyethylene, polytetrafluoroethylene (PTFE), cellulose and its derivatives, superabsorbent compounds, magnesium carbonate, calcium carbonate, polyacrylamide, porous hydroxyapatite, sawdust, fucus powder, crosslinked polyvinylpyrrolidone, calcium alginate, active charcoal, poly(vinylidene chloride/acrylonitrile) particles, in particular those sold under the general name of “Expancel®” by Akzo Nobel and under the specific references “Expancel® WE” or “DE” Expancels, and their mixtures.

Generally, the emulsion (A) and the composition (B) are formulated in a cosmetically acceptable medium.

As regards the emulsion (A), this medium comprises water and can additionally comprise one or more organic solvents.

As regards the composition (B), this medium can comprise water and/or one or more organic solvents.

Mention may be made, as organic solvent capable of being present in the emulsion (A) and the composition (B), for example, of linear or branched $C_2$-$C_4$ alkanols, such as ethanol and isopropanol; glycerol; polyols and polyol ethers, such as 2-butoxyethanol, propylene glycol, dipropylene glycol, propylene glycol monomethyl ether, diethylene glycol monoethyl ether and diethylene glycol monomethyl ether, aromatic alcohols, such as benzyl alcohol or phenoxyethanol, and their mixtures.

Such organic solvents can be present in proportions preferably of between 1 and 40% by weight, with respect to the total weight of each composition in which they are present, more preferably between 5 and 30% by weight.

Preferably, the composition (B) comprises water. More preferably, the composition (B) comprises at least 5% by weight of water, preferably at least 10% by weight of water and better still at least 20% by weight of water, with respect to its total weight.

The emulsion (A) and/or the composition (B) according to the present invention can also comprise one or more adjuvants chosen from those conventionally used in compositions for dyeing and/or bleaching keratinous fibres, such as conditioning polymers, in particular cationic conditioning polymers; thickening agents; antioxidants; penetration agents; sequestering agents; fragrances; dispersants; film-forming agents; ceramides; preservatives; or opacifying agents.

The above adjuvants can generally be present in an amount of, for each of them, between 0.01 and 20% by weight, with respect to the weight of each composition.

Another subject-matter of the present invention is a method for dyeing and/or bleaching keratinous fibres comprising the application, to the said fibres, of the agent as described above.

According to the invention, the agent applied to the keratinous fibres results from the mixing of the emulsion (A) and of the composition (B), this mixing being carried out either before application to the keratinous fibres (preparation at the time of use) or directly on the keratinous fibres (successive application to the fibres of the emulsion (A) and of the composition (B) without intermediate rinsing).

Thus, according to a first alternative form of the method according to the invention, the emulsion (A) and the composition (B) are applied, successively and without intermediate rinsing, to the dry or wet keratinous fibres.

According to a second alternative form of the method according to the invention, a composition obtained by mixing the emulsion (A) and the composition (B) at the time of use, before application, is applied to the dry or wet keratinous fibres.

In this case, the time between the mixing of the emulsion (A) and of the composition (B) and the application of the mixture to the hair then preferably does not exceed 30 minutes, preferably 10 minutes, more preferably still 5 minutes.

Independently of the alternative form employed, the ratio by weight of the amount of emulsion (A) used to the amount of composition (B) used can vary from 0.2 to 3 and preferably from 0.3 to 1.

In addition, independently of the alternative form employed, the mixture present on the fibres (resulting either from the mixing at the time of use of the emulsion (A) and of the composition (B) or from the successive application of these) is left in place for a time generally of the order of 1 minute to 1 hour, preferably of 5 minutes to 30 minutes.

The temperature during the method is conventionally between ambient temperature (between 15 and 25° C.) and 80° C., preferably between ambient temperature and 60° C.

On conclusion of the treatment, the keratinous fibres are optionally rinsed with water, optionally subjected to washing with shampoo, followed by rinsing with water, before being dried or left to dry.

Finally, another subject-matter of the invention is a dyeing and/or bleaching kit or multicompartment device comprising a first compartment including an emulsion (A) and a second compartment including a composition (B), the emulsion (A) and the composition (B) being as described above.

This device can advantageously be equipped with a means which makes it possible to dispense the desired mixture over the hair, such as the devices described in Patent FR 2586913.

This device can also comprise one or more compositions for washing and/or conditioning keratinous fibres intended to be applied before and/or after the dyeing and/or bleaching treatment according to the invention.

The following examples serve to illustrate the invention without, however, exhibiting a limiting nature.

EXAMPLE

The inverse emulsion C1 and the oxidizing composition C2 were prepared (in the tables below, the amounts are expressed in grams):

| Inverse emulsion comprising oxidation dyes | C1 |
| --- | --- |
| Liquid petrolatum | 51.5 |
| Octyldodecanol | 9 |
| Distearyldimethylammonium-modified hectorite | 1.3 |
| Propylene carbonate | 0.45 |
| Oleth-3[(1)] | 6 |
| Propylene glycol | 2 |
| Ethanol | 3 |
| Hexylene glycol | 1 |
| Dipropylene glycol | 1 |
| Monoethanolamine | 4 |
| PEO/PPO/PEO (Poloxamer: 184) | 13 |
| Ascorbic acid | 0.25 |
| 1-Methyl-2,5-diaminobenzene | 0.17 |
| 1-Hydroxy-4-aminobenzene | 0.2 |
| Resorcinol | 0.1 |
| 1-Methyl-2-hydroxy-4-((β-hydroxyethylamino)benzene | 0.25 |
| 1-Methyl-2-hydroxy-4-aminobenzene | 0.28 |
| Water | q.s. for 100 |

[(1)]HLB = 6.6

| Oxidizing composition | C2 |
| --- | --- |
| Liquid paraffin | 20 |
| $C_{16}/C_{18}$ (30/70) Cetearyl alcohol | 8 |
| 33 EO Cetearyl alcohol | 3 |
| Oxyethylenated (4 EO) rapeseed amides | 1.5 |
| Vitamin E | 0.1 |
| Glycerol | 1 |
| Hydrogen peroxide | 6 |
| Sodium stannate hexahydrate | 0.04 |
| Diethylenetriaminepentaacetic acid | 0.015 |
| Tetrasodium pyrophosphate decahydrate | 0.03 |
| Phosphoric acid | q.s. for pH = 3 |
| Demineralized water | q.s. for 100 |

The oxidizing composition C2 corresponds to a composition (B) in accordance with the present invention.

At the time of use, one part by weight of composition C1 is mixed with one part by weight of composition C2.

The mixture is subsequently applied to locks of hair comprising 90% natural white hairs. After a leave-in time of 30 minutes at ambient temperature (23° C.), the hair is rinsed, washed with a standard shampoo and then dried. A mahogany blonde colouring is then obtained.

The invention claimed is:

1. Agent for dyeing and/or bleaching keratinous fibres, comprising:

a water-in-oil emulsion (A) comprising one or more basifying agents, water, one or more surfactants having an HLB of less than 8, chosen from oxyalkylenated and/or glycerolated nonionic surfactants, and from 30 to 70% by weight, with respect to the total weight of the emulsion (A), of one or more oils not comprising a carboxylic acid functional group, and a second composition (B) comprising one or more oxidizing agents, the total amount of oil(s) not comprising a carboxylic acid functional group in the mixture of the emulsion (A) and of the composition (B) representing at least 20% by weight, with respect to the total weight of the mixture of these two compositions.

2. Agent according to claim 1, characterized in that the basifying agent is chosen from aqueous ammonia, alkaline carbonates, sodium hydroxide, potassium hydroxide and organic amines selected from the group consisting of alkanolamines and their derivatives, and the compounds of following formula (I):

(I)

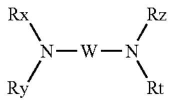

(I)

in which W is a $C_1$-$C_6$ alkylene residue optionally substituted by a hydroxyl group or a $C_1$-$C_6$ alkyl radical and Rx, Ry, Rz and Rt, which are identical or different, represent a hydrogen atom or a $C_1$-$C_6$ alkyl, $C_1$-$C_6$ hydroxyalkyl or $C_1$-$C_6$ aminoalkyl radical.

3. Agent according to claim 1, characterized in that the oxidizing agent is chosen from hydrogen peroxide, urea hydrogen peroxide, alkali metal bromates or ferricyanides, peroxygenated salts selected from the group consisting of alkali metal or alkaline earth metal persulphates, perborates and percarbonates, oxidation/reduction enzymes selected from the group consisting of laccases, peroxidases and 2-electron oxidoreductases, optionally in the presence of their respective donor or; and is preferably hydrogen peroxide.

4. Agent according to claim 1, characterized in that the emulsion (A) comprises from 40 to 65% by weight of one or more oils not comprising a carboxylic acid functional group, with respect to the total weight of the emulsion (A).

5. Agent according to claim 1, characterized in that the total amount of oil(s) not comprising a carboxylic acid functional group in the mixture of the emulsion (A) and of the composition (B) is between 20.5 and 75% by weight, with respect to the total weight of the mixture of these two compositions.

6. Agent according to claim 1, characterized in that the oil or oils not comprising a carboxylic acid functional group are chosen from hydrocarbons, non-silicone oils of animal, vegetable, mineral or synthetic origin, fatty alcohols, fatty acid and/or fatty alcohol esters, silicones and their mixtures.

7. Agent according to claim 1, characterized in that the emulsion (A) comprises from 1 to 20% by weight of one or more surfactants having an HLB of less than 8 with respect to the total weight of the emulsion (A).

8. Agent according to claim 1, characterized in that the said surfactant or surfactants chosen from oxyalkylenated and/or glycerolated nonionic surfactants have an HLB of less than or equal to 7.

9. Agent according to claim 1, characterized in that the said surfactant or surfactants having an HLB of less than 8 chosen from oxyalkylenated and/or glycerolated nonionic surfactants belonging to the following families:

oxyethylenated alkylphenols,
ethylene oxide/propylene oxide condensates,
oxyethylenated vegetable oils,
oxyethylenated fatty alcohols,
esters of fatty acids and of polyethyleneglycols,
polyoxyethylenated esters of fatty acids and of sorbitol.

10. Agent according to claim 1, characterized in that the emulsion (A) additionally comprises one or more oxidation dyes chosen from oxidation bases, optionally in combination with one or more couplers.

11. Agent according to claim 1, characterized in that the emulsion (A) additionally comprises one or more direct dyes.

12. Agent according to claim 1, characterized in that the emulsion (A) and the composition (B) do not comprise a direct dye or an oxidation dye (bases and couplers) or else, if they are present, their total content does not exceed 0.005% by weight, with respect to the total weight of each composition.

13. Method for dyeing and/or bleaching keratinous fibres comprising the application of the emulsion (A) and of the composition (B) as defined in claim 1, successively and without intermediate rinsing, to the said dry or wet fibres.

14. Method for dyeing and/or bleaching keratinous fibres comprising the application of a composition, obtained by mixing at the time of use the emulsion (A) and the composition (B) as defined in claim 1, to the said dry or wet fibres.

15. Dyeing and/or bleaching kit or multicompartment device comprising a first compartment including an inverse emulsion (A) and a second compartment including a composition (B), the inverse emulsion (A) and the composition (B) being as defined in claim 1.

* * * * *